United States Patent
Empie et al.

(10) Patent No.: US 6,399,072 B1
(45) Date of Patent: *Jun. 4, 2002

(54) METHOD OF PREPARING AND USING ISOFLAVONES FOR THE TREATMENT OF ALCOHOLISM

(75) Inventors: Mark Empie, Forsyth; Eric Gugger, Latham, both of IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/615,152

(22) Filed: Jul. 13, 2000

Related U.S. Application Data

(62) Division of application No. 09/162,038, filed on Sep. 28, 1998, now Pat. No. 6,261,565, which is a continuation-in-part of application No. 09/035,588, filed on Mar. 5, 1998, now Pat. No. 6,033,714, which is a continuation-in-part of application No. 08/868,629, filed on Jun. 4, 1997, now Pat. No. 5,792,503, which is a division of application No. 08/614,545, filed on Mar. 13, 1996, now Pat. No. 5,702,752.
(60) Provisional application No. 60/060,549, filed on Oct. 2, 1997.

(51) Int. Cl.$^7$ .............................................. A01N 65/00
(52) U.S. Cl. ...................... 424/195.1; 514/783; 514/26; 514/25; 514/27; 514/568; 514/717; 514/726
(58) Field of Search ....................... 424/195.1; 514/783, 514/26, 25, 27, 568, 717, 726

(56) References Cited

U.S. PATENT DOCUMENTS

| | | | |
|---|---|---|---|
| 4,350,688 A | | 9/1982 | Schmittmann |
| 4,428,876 A | | 1/1984 | Iwamura |
| 4,557,927 A | | 12/1985 | Miyake et al. |
| 5,032,580 A | | 7/1991 | Watanabe et al. |
| 5,554,645 A | | 9/1996 | Romanczyk, Jr. et al. |
| 5,952,374 A | * | 9/1999 | Clarkson, Jr. et al. ...... 514/456 |
| 6,261,565 B1 | * | 7/2001 | Empie et al. ............ 424/195.1 |

FOREIGN PATENT DOCUMENTS

| | | | |
|---|---|---|---|
| CN | 1080863 | * | 1/1994 |
| CN | 1080864 | * | 1/1994 |
| EP | 0 348 781 A2 | | 6/1989 |
| EP | 0 795 553 A1 | | 9/1997 |
| JP | HEI 02-261365 | | 10/1990 |
| JP | HEI 04-152845 | | 5/1992 |
| JP | HEI 04-506403 | | 11/1992 |
| JP | HEI 07-147903 | | 6/1995 |
| JP | HEI 08-73369 | | 3/1996 |
| JP | HEI 10-179100 | | 7/1998 |
| JP | Hei 01-312965 | | 12/1998 |
| JP | HEI 11-12172 | | 1/1999 |
| WO | WO 93/23069 | | 11/1993 |
| WO | WO-9323069 | * | 11/1993 |
| WO | WO 95/03816 | | 2/1995 |
| WO | WO 95/10512 | | 4/1995 |
| WO | WO 97/07811 | | 6/1997 |
| WO | WO 97/32593 | | 9/1997 |
| WO | WO-9958124 | * | 11/1999 |

OTHER PUBLICATIONS

Naik et al., "An in vitro and in vivo study of antitumor effects of Genistein on hormone refractory prostate cancer." Anticancer Research, 14:2617–2620 (1994).*
Messina et al., "Soy intake and cancer risk: A review of the in vitro data." Nutrition and cancer, 21(2), 113–31, 1994.*
Barnes et al. "Rationale for the use of genistein–containing soy matrices in chemoprevention trials for breast and prostate cancer." J. Cellular Biochem, Supp. 22:181–187, 1995.*
Coward et al. "Genistein, Daidzein, and their B–glycoside conjugates: Antitumor isoflavones in soybean foods from american and asian diets. " J. Agric. Food Chem., 41, 1961–1967, 1993.*
Keung et al. "Therapeutic lessons form traditional oriental medicine to contemporary occidental Pharmacology." Abstract:EXS, 71, 371–81, 1994.*
Article: No. XP–002096529 "Saponins as Anticarcinogens", "The Journal of Nutrition", by Rao, A. V. and Sung, M.K.
English translation of relevant material re Patent Appln. Laid Open Nos. (1) Hei 02–261365; (2) Hei 01–312965; (3) Hei 04–152845; (4) Hei 08–73369; (5) Hei 07–147903; (6) Hei 04–506402; (7) Hei 10–179100; and (8) Hei 11–12172.
Article: No. XP–00209653 "Dietary Soybean Protein Prevents Bone Loss in an Ovariectomized Rat Model of Osteoporosis", "The Journal of Nutrition", Arjmandi, B. H. et al.
European Patent Office, Patent Abstract of Japan Publication No. 07304655 dated Nov. 21, 1995 for JP 59085265.
Abstract of Japanese Publication No. 07304655 dated Nov. 21, 1995 for JP 4283518.
Abstract of Japanese Publication No. 07304655 dated Nov. 21, 1995 for JP 61100524.
Abstract of Japanese Publication No. 07304655 dated Nov. 21, 1995 for JP 07304655.

* cited by examiner

*Primary Examiner*—Ralph Gitomer
*Assistant Examiner*—Devesh Khare
(74) *Attorney, Agent, or Firm*—Michael Best & Friedrich LLC; J. Warren Whitesel

(57) ABSTRACT

A composition is prepared by extracting phytochemicals from plant matter for treatment of alcohol dependency. This composition is enriched preferably with two or more fractions of plant matter, namely: isoflavones, lignans, saponins, sapogenins, catechins and phenolic acids. Soy is the preferred source of these chemicals; however, other plants may also be used, such as wheat, psyllium, rice, oats, red clover, kudzu, alfalfa, flax, and cocoa. The composition is a dietary supplement for treatment of alcoholism. The isoflavone may be any in a group including malonyl, acetyl, glucoside, and aglycone. The composition is in a concentrated form to be delivered in an easy to consume dosage, such as a pill, tablet, liquid, capsule, or a food supplement including a health bars.

10 Claims, No Drawings

METHOD OF PREPARING AND USING ISOFLAVONES FOR THE TREATMENT OF ALCOHOLISM

This is a division of Ser. No. 09/162,038, filed Sep. 28, 1998 (a formal application which replaced provisional application Serial No. 60/060,549 filed Oct. 2, 1997) now U.S. Pat. No. 6,261,565, which in turn, is a continuation-in-part of Ser. No. 09/035,588, filed Mar. 5, 1998, now U.S. Pat. No. 6,033,714, which in turn, is a continuation-in-part of Ser. No. 08/868,629, filed Jun. 4, 1997, now U.S. Pat. No. 5,792,503, which in turn, is a division of Ser. No. 08/614,545, filed Mar. 13, 1996, now U.S. Pat. No. 5,702,752.

This invention relates to compositions extracted from vegetable matter and more particularly to phytochemicals, including saponogenins and saponins, lignans, phenolic acids, catechins and isoflavones, and especially those extracted from a family of plants including soy, flax, tea, and cocoa and methods of using these compositions as nutritional supplements or food additives.

BACKGROUND

As used herein, the term "isoflavone" includes malonyl, acetyl, glucoside, and aglycone forms of the isoflavones.

Alcoholism is, perhaps, the most widespread addiction which is responsible for more deaths than the rest of the addictive drugs combined. It is also one of the addictions which is the most difficult to overcome. It is thought that one of the more successful treatments for helping recovering alcoholics is a use of a phytochemicals, especially isoflavones, as a source of supplemental hormones. However, it is also thought that there are superior results when a plurality of such phytochemicals are consumed in combinations.

A proper diet should contain the desired phytochemicals. However, a trouble is that many people do not have or do not like the proper kind of diet which provides the desirable effects. Hence, the problem is to furnish the necessary food values in some other form.

Plant materials are known to contain a number of classes of organic low molecular weight compounds which exert bioactivity in various animals. Historically, these compounds have been considered to be somewhat non-nutritive however, recent scientific evidence now suggests these compounds may play an important role in the maintenance of health, in chemoprevention, and in the mitigation of certain conditions or diseases associated with the circulation of sex hormones, including sleep disorders and vaginal dryness.

Edible plants normally contained in the diet, or materials used as herbal remedies/dietary supplements, may contain collections of structurally related compounds. These related substances are often unique in their amounts and distribution when compared among various plant sources. The most notable groups of compounds exhibiting bioactivity are known as flavonoids, isoflavones, saronins, lignans, alkadoids, catechins and phenolic acids.

Epidemiology studies relating diet to disease suggest that dietary components may predispose populations to reduced risk of certain diseases. Far eastern populations consuming soy have reduced rates of breast, prostate and colon cancers and coronary heart disease, while populations in Finland have reduced rates of prostate cancer. Researchers are just now studying the specific compounds in the diet to understand the basis for the epidemiological observations.

Among the various plants consumed in the diet, several are rich sources of phytochemicals. Soy products contain high amounts of isoflavones and saponins. Unrefined diet grains include plants such as wheat, psyllium, rice, flax and oats that contain lignans. Cocoa contains catechins and phenolic acids. Certain non-dietary plants are also sources of the same chemical molecules, such as lignans and isoflavones in kudzu root or red clovers. Isoflavones and lignans act as weak estrogenic substances. Tea plants are also a rich source of phytochemicals, including catechins and phenolic acids.

Isoflavones can be used alone to treat or prevent breast cancer, prostate cancer, skin cancer, and colon cancer or as mechanism inhibitors. Isoflavones alone may also reduce or prevent various symptoms related to the onset and duration of menopause, including hot flashes and osteoporosis. Isoflavones alone may also be effective in certain cardiovascular applications, including heart disease, reducing cholesterol-lipid levels, modulating angiogenesis, and other vascular effects. Moreover, isoflavones alone have been implicated in reducing headaches, dementia, inflammation, and alcohol abuse, as well as imnunomodulation.

Lignans alone have been implicated in preventing or treating breast cancer, prostate cancer and colon cancer as well as reducing hot flashes, preventing osteoporosis and showing antiviral potential. Lignans also have antimitotic and fungicidal activity. A plant lignan, the catecholic nordihydro-guaiaretic acid, was a potent antioxidant once used by the food industry.

Saponins alone have been implicated in preventing or treating skin cancer, colon cancer, reducing serum cholesterol, and in immunomodulation and antiviral activity. Saponins also exhibit antioxidant effects and act as free radical scavengers.

Phenolic acids have shown antioxidant activity.

People who eat a high soy diet show reduction of many of these above-discussed symptoms. This suggests that ingesting a combination of these phytochemicals in a ratio such as that found in soy may result in an additive or synergistic effect. However, a high soy diet has some undesirable effects, including flatulence, undesirable taste, and hesitancy among Western consumers to change their lifestyle to incorporate soy in their diets, even for such benefits.

Isoflavones, which are heterocyclic phenols, are understood to include the soy compounds genistin, daidzin and glycitein, as well as biochanin A, equol, formononetin, and o-desmethylangolensin and natural derivatives thereof. These compounds and their aglycone or de-methylated aglycone forms, such as genistein and daidzein, are believed to have similar activities once they are ingested. They are sometimes referred to as phytoestrogens.

Lignans are defined to be compounds possessing a 2,3-dibenzylbutane structure. They include matairesinol, secoisolariciresinol, lariciresinol, isolariciresinol, nordihydroguaiaretic acid, pinoresinol, olivil, other compounds which may be precursors of enterolactone and enterodiol and modifications thereof, including diglucosides.

Phenolic acids include p-hydrobenzoic acid, proto chuic acid, and vanillic acid. Other phenolic acids are chlorogenic acid, caffeic acid, ferulic acid, gallic acid, sinapic acid, syringic acid, coumaric acid, cinnamic acid, gentisic acid, salicylic acid, hydroxy benzoic acid and hydroxy phenyl acetic acids and derivatives. This list of phenolic acids should be understood to include the various isomers and derivatives found in the natural vegetable source.

Catechins, or flavan-3-ols, include epigallocatechin, catechin, epicatechin and gallocatechin.

Saponozenins are C-27 sterols in which the side chiain has undergone metabolic changes to produce a spiroketal.

Saponogenins occur naturaily as saponins, which are 3-O-glycosides of the parent steroid or triterpenes. Digitonin from Digitalis is a saponin. Saponins include clucosides of sapogenin such as triterpenoids or steroids and saccharides such as glucose, arabinose, galactose or glucuronic acid. Typical examples of leguminous saponins are glycyrrhizin (glycyrrhetinic acid+glucuronic acid) contained in *Glycyrrhiza glahra*, soysaponin contained in soybean and alfalfasaponin contained in *Medicago sativa*. Saponins also include chemical entities identified as triterper phenols such as tomatine, soyasapogenols A, B, C, D, E and F, ginsengoside fraction 3 and 4, medicagenic acid, hederagenin, glycyrrhizin digitonin, quillaja saponin, lucernic acid and zahnic acid. The natural modifications of these compounds found in the vegetable source are also included in this identification.

A need exists for an improved composition consisting substantially of isoflavones, lignans, saponogenins, saponins, and/or phenolic acids which will produce improved results over any of these taken alone. Furthermore, a need exists for a composition in which the beneficial phytochemicals are enriched as compared to their original source. This permits individuals to conveniently consume such phytochemicals as a nutritional supplement or as a food additive.

SUMMARY OF THE INVENTION

An object of this invention is to provide a convenient way for individuals to consume isoflavones, litgnans, saponins, catechins and/or phenolic acids, either as a nutritional supplement or as an ingredient in a more traditionai type of food including health bars.

An other object of this invention is to provide an optimized extract composition of phytochemicals which is in sufficient concentration to be delivered in an easy to consume dosasge such as a pill, tablet, capsule, liquid or ingredient in a food.

Yet another object of this invention is to prepare the phytochemical extract to be delivered as a topical application in a cream or lotion. In this form, the isoflavones, lignans, saponins, catechins and/or phenolic acids are dispersed and suspended in a suitable liquid or gel matrix to render a stable cream or lotion as the delivery vehicle.

A further object of this invention is to provide an extract concentrate which is closely similar in chemical composition to the chemical entities tound in the natural plant source.

In keeping with this aspect of the invention, the isoflavones, lignans, saponins, catechins and/or phenolic acids are extracted from a suitable vegetable source to render a composition which is substantially more concentrated than the original material and by more than 5 times in one or more of the desired bioactive components.

This extract may be used alone or combined with one or more other plant extracts to produce the optimized composition. Further, this extract composition may be formulated with one or more other dietary nutrients, such as vitamins, minerals, amino acids, etc., to provide a nutritional supplement further optimized for a desired health effect. All these ingredients may be combined with necessary binders, excipients, preservatives, colors and the like known to those in the industry in order to produce a suitable tablet, capsule, pill, liquid, cream, powder or food ingredient including health bars.

These phytochemicals may be packaged and provided in final form by means known to the supplements and food ingredient industries. The materials are intended to provide health and well-being benefits.

DETAILED DESCRIPTION OF THE INVENTION

The improved composition is obtained by fractionating a plant source high in isoflavones, lignans and other phytochemicals such as defatted soybean flakes, soy molasses, soy whey, red clover, alfalfa, flax, cocoa, tea, or kudzu root. These may be fractionated along or in combination with these other plants known to be high in the various isoflavones, lignans, saponins, catechins and phenolic acids. The fractionation results in substantially removing water, carbohydrates, proteins, and lipids from the source material. The fractionation method may be preferably that disclosed in U.S. Pat. Nos. 5,702,752; 6,017,555; 6,033,714; or 4,428,876, or an extraction using ethyl acetate or n-butanol may be used. U.S. Pat. Nos. 5,702,752; 6,017,555; 6,033,714 is assigned to the assignee of this invention.

Other extraction processes, which may be used alone or in combination, include differential solubility, distillation, solvent extraction, adsorptive means, differential molecular filtration and precipitation.

The preferred composition is an improvement over known commercial materials regarding the amount of phytochemicals per gram of substance and the amounts of different phytochemicals present which affect physiologic function.

These natural substances have been consumed in food sources for long periods of time and more closely relate to the substances consumed which provide the basis for the epidemiological evidence for health benefits. Additional benefits may be derived from improved physical properties relative to phytochemicals chemically modified from their original food source form.

The resulting composition is expected to comprise in a preferred form: between 5% and 95% isoflavones, between 0% and 70% lignans, and between 2% and 70% saponins and sapogenins. In a more preferred form, the composition will be extracted from soy. In another preferred form, the composition will contain a ratio of (saponins plus saponogenins) to isoflavones from 1:100 to 100:1, with the isoflavones consisting predominantly of naturally occurring derivatives of genistein and/or its precursor biochanin A and daidzein and/or its precursor formononetin, with a ratio of the genistein derivatives to daidzein derivatives from 100:1 to 1:100. Preferably, the isoflavones are predominantly glycosylated derivatives.

The composition's ratios may be readily varied by changing the plant source or by combining several plant sources for extraction. Thus, as further study shows which phytochemical combinations are more efficacious for certain health effects, the particular composition will also vary.

It is known that isoflavones, lignans, and saponinst can be used advantageously to treat or prevent various cancers, including breast cancer, prostate cancer, skin cancer, and colon cancer.

It is believed that the improved composition will provide increased benefits in the form of chemoprevention. Recent experiments appear to confirm this belief.

EXAMPLE 1

An initial series of animal studies was made to investigate the effects of dietary soy products on the growth of s.c. (SUBCUTANEOUS) implanted LNCaP in male SCID mice. A high isociavone-containing soy protein isolate (SPI) (2.0 mg isoflavones/g SPI) is provided by Protein Technology International (St. Louis, Mo.) A soy phytochemicals extract, soy phytochemicals concentrate (SPC) which contains 28 5% total soy isoflavones and a diverse amount of other soy phytochemicals, is provided by Archer Daniels Midland Company (Decatur, Ill.). These materials were used to prepare six experimental diets. Table 1 shows ingredients of the diets.

Eight-week-old male SCID mice were s.c. injected on the right flank with $2 \times 10^6$ LNCaP cells from hosts, randomized into six groups (n=10) and assigned to one of the experimental diets. Food intake, body weight, and tumor volume were measured. At the termination of the experiment, blood samples were collected and serum separated for PSA analysis. An aliquot of tumor tissues was formalin-fixed, paraffin-embedded, and cut into 4 μm sections for in situ histochemical detection of apoptotic cells, and immunohistochemical analyses of angiogenesis and proliferation. Another aliquot was prepared for cell lysates for western blot to determine the expression of apoptosis-related gene products.

Table 2 summaries the effects of treatment on food intake body weight, isoflavone intake and tumor volume. Soy products did not significantly, after food intake or body weight. Compared to casein-fed controls, tumor volumes from mice treated with SPI (20%), SPC (1.0%), and SPI and SPC (1.0%) were reduced by 12%, 28% (P<0.04), or 40% (P<0.005), respectively. Factorial analysis indicated that there was no significant effect of protein source on tumor growth. Linear regression analysis indicated that tumor volumes were inversely correlated to total dietary isoflavones (Tumor volume $(cm^3) = -0008 + 2.121 \times Isoflavones$ (mg), $R^2 = 0.76$, p<0.03).

Table 3 shows the effects of SPC at 1.0% of the diet on apoptosis, proliferation, and angiogenesis of tumors from a pilot study. It indicates that dietary supplementation of soy phytochemicals inhibits the growth of LNCaP tumor in vitro by enhancing apoptosis and inhibiting proliferation of tumor cells. Its inhibitory effect on tumor angiogenesis is not significant which may be due to small sample size (n=2)

Results from in vitro study showed that genistein and soy phytochemical concentrate inhibited secretion of PSA by LNCaP cells into media. PSA concentrations were reduced 68% and 74% by 25 and 50 uM of genistein treatment respectively, and 31% and 42% by 25 and 50 μM of soy phytochemical concentrate treatment respectively.

TABLE 1

Ingredients of experimental diets (grams)

| | Diet 1 casein | Diet 2 SPI | Diet 3 Casein/ LSPC | Diet 4 SPI/ LSPC | Diet 5 Casein/ HSPC | Diet 6 SPI/ HSP |
|---|---|---|---|---|---|---|
| SPI | 0 | 200 | 0 | 200 | 0 | 200 |
| Casein | 200 | 0 | 200 | 0 | 200 | 0 |
| DL-methionine | 3 | 3 | 3 | 3 | 3 | 3 |
| Corn starch | 150 | 150 | 150 | 150 | 150 | 150 |
| Sucrose | 500 | 500 | 500 | 500 | 500 | 500 |
| Cellulose, BW200 | 50 | 50 | 50 | 50 | 50 | 50 |
| Corn oil | 50 | 50 | 50 | 50 | 50 | 50 |
| Mineral Mix, S10001[1] | 35 | 35 | 35 | 35 | 35 | 35 |
| Vitamin Mix, V10001[1] | 10 | 10 | 10 | 10 | 10 | 10 |
| Choline Bitartrate | 2 | 2 | 2 | 2 | 2 | 2 |
| Soy phytochemicals | 0 | 0 | 2 | 2 | 10 | 10 |
| Total (g) | 1000 | 1000 | 1002 | 1002 | 1010 | 1010 |
| (isoflavones, mg/kg diet) | 0 | 245 | 341 | 586 | 705 | 950 |

[1]AIN formulation with minor modification by DR. E. A. Ulman, Research Diets, Inc.

TABLE 2

Final body weight, total food intake, total isoflavone intake, and tumor volume

| Treatment | Body weight | Food intake grams/m | Total isoflavone | Tumor volume $(cm^3)$ |
|---|---|---|---|---|
| Casein | 22.4 ± 0.5[1] | 46.6 ± 3.1 | 0.00 ± 0.00 | 2.32 ± 0.31[2] |
| SPI | 23.1 ± 0.7 | 46.2 ± 2.8 | 17.00 ± 6.37 | 2.06 ± 0.32 |
| Casein/LSPC | 21.4 ± 0.7 | 41.2 ± 3.4 | 14.03 ± 14 | 1.88 ± 0.35 |
| SPI/LSPC | 22.6 ± 0.6 | 50.1 ± 4.7 | 29.36 ± 2.76 | 1.66 ± 0.29* |
| Casein/HSPC | 22.2 ± 0.7 | 44.8 ± 6.1 | 76.38 ± 10.40 | 1.64 ± 0.22* |
| SPI/HSPC | 22.0 ± 0.6 | 47.5 ± 1.7 | 92.53 ± 3.22 | 1.39 ± 0.30** |

[1]Values are means ± SE. There are no significant differences of food intake or body weight among treatment groups.
[2]Compared with control group, SPI/LSPC, casein/HSPC, and SPI/HSPC had significantly smaller tumor volumes (*p < 0.04, **p < 0.005)

TABLE 3

Effects of treatment on apoptotic index (AI, % TUNEL), proliferation index (PI, % PCNA Staining) and angiogenesis (microvessel density)

| Treatment | AI (% TUNEL) | PI (% PCNA) | Microvessel Density |
|---|---|---|---|
| Control (n = 2) | 6.07 ± 0.88 | 60.1 ± 1.1 | 12.5 ± 3.8 |
| Casein/HSPC (n = 2) | 10.75 ± 0.54 | 51.7 ± 1.3 | 9.7 ± 0.7 |
| P value | <0.02 | <0.01 | >0.05 |

Values are means±SE.

In summary, preliminary results indicate that soy products inhibit the s.c. growth of LNCaP tumor in SCID mice, possibly via induction of apoptosis, and inhibition of angiogenesis and proliferation.

Isoflavones or lignans can alleviate menopausal-related symptoms such as hot flashes and osteoporosis as well as alleviate symptoms associated with menstruation. This is further believed to be due to their estrogenic activity. It is believed that the improved composition described here will alleviate these symptoms even more effectively.

Also, isoflavones positively affect various cardiovascular-related conditions, including heart disease, cholesterol (saponins also positively affect cholesterol), angiocenesis and other vascular effects. It is believed that the improved composition will produce results for these cardiovascular conditions at least as beneficial as those hitherto known and at a reduced cost.

As explained earlier, isoflavones, lignans, and saponins are known to individually positively affect various neurological and immunological symptoms. It is believed that the improved composition will result in alleviating neurological and immunological symptoms at least as well as those compounds hitherto known and at a reduced cost. Moreover, it would be expected that some synergism would arise out of the combination described herein.

The improved composition may be administered orally, pareriterally, for instance, subcutaneously, intravenously, intramuscularly, intraperitoneally, by intranasal instillation or by application of an aerosol spray to mucous membranes, or to the skin by an ointment or a cream.

Administering the improved composition may be done with any suitable carrier, in solid or liquid dosage form such as tablets, capsules, powders, soft gels, solutions, suspensions, emulsions, ointments, or creams. The improved composition may also be administered as a food supplement or as a food ingredient.

The amount of the improved composition administered will vary depending on the person, the mode of administration, and the desired result. An effective amount is expected to be 10 mg to 2000 mg/per dose.

EXAMPLE 2

Tablet Manufacture

The composition provided for in this patent may be used to prepare tablets or other dosage forms. An example of a capsule preparation is provided in Example 2. The higher the concentration of the active component, the easier it is to form a tablet or emulsion. This leads to an added ability to incorporate other dietary nutrients. An example would be to prepare a phytochemical tablet which incorporates calcium and vitamin E as a supplement to maintain bone health and/or reduce post menopausal symptoms such as hot flashes. In an example of this embodiment, a 600 mg dry compression tablet was prepared containing a total of 125 mg of isoflavones concentrate (50 mg isoflavone compound). Included in the tablet formulation was a source of calcium and magnesium.

Dry compression tablets were produced by first blending the following ingredients: 4 kg of the improved composition (39.83% isoflavones), 1.91 kg sorbitol, 0.095 kg magnesium stearate, and 13.11 kg dicalcium phosphate in a 120 quart capacity Hobart mixer. This blend of ingredients was then dry compressed at 1 ton pressure with a Stokes BB2 simple press into tablets having a total weight of 600 mg containing 125.53 mg of the improved composition and therefore 50 mg of total isoflavones.

Aternatively, a photochemical concentrate may be provided in a single dosage form, a skin cream or as a food ingredient added to conventional food in amounts from 10 mg to 2000 mg/per dose, the purpose of which is to exert a positive effect on health and well being. These benefits include: cancer prevention, estrogen and sex hormone related maladies, inhibition of the pituitary-thyroid-gonadotrophic axis, alcohol dependency reduction, modulation of the cardiovascular, immune and nervous systems, antiviral effects and analgesic effects:

EXAMPLE 3

Two-piece gelatin capsules were produced by filling the receiving end of the empty size "0" capsules with 0.106 g of the improved composition (44.35% isoflavones) and closed with the capping end, providing a capsule containing 47.2 mg of total isoflavones.

EXAMPLE 4

A comparison between various sources of phytochemical preparations is given in Table 4. It is readily seen that the phytochemical components of the composition of the "Isoflavone Concentrate" of this invention is substantially higher than the corresponding amounts in the natural vegetable materials. Notably, the amount of glycone isoflavones and saponins are over 100 times more concentrated compared to the food source and over twenty times more concentrated compared to the germ of the plant which naturally concentrates these phytochemicals. Comparison of the "Isoflavone Concentrate" of this invention to other concentrates shows that the isoflavone fraction predominates in these latter products, reducing the amount of other healthful phytochemicals. Additionally, the extraction methods of these other products employ techniques which modify the components, particularly the isoflavones, so that they are not identical to the substances found in the natural vegetable material (U.S. Pat. No. 5,637,562).

One version of the improved composition was compared to other previously described compositions. The results are shown in Table 4

TABLE 4

Comparative Products to the Invention

| Product Example | Isoflavone Glycosides in Product (mg/g) | Isoflavone Aglycones in Product (mg/g) | Genistein/ Daidzein Ratio | Lignans (mg/g) | Saponins (mg/g) | Phenolic Acids (mg/g) |
| --- | --- | --- | --- | --- | --- | --- |
| Improved composition | 401.0 | 3.37 | 1.06 to 1 | 0.2 | 460.7 | 25.47 |
| Soybean | 1.748–2.776[a] | 0.044[a]–0.075 | 1.59–2.7 | NA | 0.9–3.2[b] | |
| Soy Flour (defatted) | 1.969[a] | 0.045[a] | 3.58 | 0.0013 | | 2.870[c] |
| Soy germ | 24.32[d] | 0.85[d] | | NA | 16.7–1.98[b] | NA |
| Product[e] patent (PTI) | NA | 2.5–6.5[e] | 0.5–3.5 | NA | NA | NA |
| Product[f] patent (PTI) | NA | 5.1–14.7[1] | 0.433–3.48 | NA | NA | NA |
| Product[g] patent (PTI) | NA | 1.7–3.5[g] | 0.66–2.86 | NA | NA | NA |
| PTI product[h] | NA | 970 | 12.8 | NA | NA | NA |
| PTI product[h] | NA | 640 | 2.0 | NA | NA | NA |
| Soy Molasses (dried) | 27.6 | 0.1 | 1.37 | NA | NA | 5.788 |
| Novogen[i] | 0.0 | 550 | 1–1.7 to 1 | NA | NA | NA |

[a]Wang H. and Murphy P. A., J. Agric. Food Chem 1994, 42, 1666–1673.
[b]Anderson R. L. and Wolf W. J., J. Nutr 125:581S–588S, 1995
[c]Seo A. and Morr C. V., J. Agric. Food Chem 1984, 32, 530–533.
[d]Soy Life ™ promotional literature
[e]WO 95/10530, PCT/US94/10697
[f]WO 95/10512, PCT/US94/10699
[g]WO 95/10529, PCT/US94/10696
[h]NCI paper
[i]Novogen promotional literature

EXAMPLE 5

The improved composition, containing the glycoside forms of isoflavones, has as one aspect an improved solubility at body temperature over the previously described compositions containing the aglycoside forms.

Separate solutions (0.02% in distilled water) were made for genistein, genistin, daidzein, daidzin, and isoflavone concentrate in volumetric flasks. Samples were then placed in a 37° C. water bath for 17 hours, followed by rapid filtration through a 0.2 micron syringe-type filter to remove particulates. Filtered samples were then analyzed for isoflavone concentration by HPLC. Results are tabulated as shown in Table 5.

TABLE 5

Differential Solubility of Isoflavone Glycosides vs. Aglycones

| Isoflavone sample | Genistein (ppm) | Genistin (ppm) | Daidzein (ppm) | Daidzin (ppm) |
|---|---|---|---|---|
| Genistein | 7.42 | | | |
| Genistin | | 33.89 | | |
| Daidzein | | | 3.64 | |
| Daidzin | | | | 48.51 |
| Isoflavone Concentrate | 0.492 | 30.075 | 0.672 | 37.69 |

The glycoside forms, genistin and daidzin, are at least 457 and 13.32 fold higher in concentration at 37° C. than their corresponding aglycone forms, respectively.

The modifications made to the isoflavones are to remove the carbohydrate attached to the isoflavone moiety. This modification renders the isoflavone less soluble in water. Maintenance of the natural modification, glycosylation, enhances solubility. This fact is shown in the comparative solubility chart of Table 5. This chart shows that the genistin isoflavone is 4.6 times higher and the daidzin isoflavone is 13.3 times higher than the corresponding non-glycosylated form. Higher solubility can lead to better bioavailability to intestinal organisms. The glycosylation does not inhibit absorption in the gut because the intestinal microflora convert the glycone form to the aglycone form before absorption occurs.

EXAMPLE 6
Extraction of Lignans from Flax

Lignans can be readily extracted from flax using this following method.

978 g of defatted flax meal (F1) was extracted with 2000 g of 85% ethanol at 40° C. for 10 minutes, forming a slurry. The resulting slurry was filtered and extraction was repeated twice with a total of 6000 g of ethanol.

The ethanolic fraction was then evaporated under vacuum at 70° C., resulting in an aqueous fraction of 1186 g. The aqueous fraction was combined with 1000 g of water and mixed.

The mixed sample was then ultra-filtered through a 5000 molecular weight cutoff membrane, resulting in a 767 g permeate fraction and a retentate fraction of 1283 g.

The retentate fraction was freeze-dried, resulting in a 27.84 g sample (F2).

The 767 g permeate fraction at 50° C. was fed to a 35 ml bed volume, XAD-4 resin column at a rate of 10 ml/min. The column effluent was collected and dried, resulting in a 14.8 g sample (F3). XAD-4 is a trademark for an absorbent resin, available from Rohm & Haas.

The column was then eluted with four bed volumes (140 ml) of 70% ethanol at 50° C. The eluent sample was evaporated under vacuum at 70° C. and dried, resulting in a 1.79 g sample (F4). The four fractions were then analyzed for their lignan content, measured as the concentration by weight of secoisolariciresinol. As Table 6 shows, this extraction method enriches lignan concentration.

TABLE 6

| LIGNAN CONCENTRATIONS AS SECOISOLARICIRESINOL | | | | |
|---|---|---|---|---|
| FRACTION | F1 | F2 | F3 | F4 |
| SECO. CONC. (mg/g) PHENOLIC ACID | 2.3 | 1.9 | 4.8 | 13.4 |

While the present invention has been disclosed in terms of the preferred embodiment in order to facilitate a better understanding of the invention, it should be appreciated that the invention can be embodied in various ways without departing from the principles of the invention. Therefore, the invention should be understood to include all possible embodiments, modifications, and equivalents to the described embodiment which do not depart form the principles of the inventions as set out in the appended claims.

What is claimed is:

1. A composition for treatment of medical conditions resulting from alcohol dependency involving the brain and nerves, said composition being made from a plant matter in which the composition is a medicament enriched in at least two of the phytochemicals selected from the group consisting of isoflavones, lignans, saponins, catechins and phenolic acids, said medicament having an effective amount of phytochemicals selected on a basis of a therapeutic treatment for alcohol dependency.

2. The composition of claim 1 in which the ratio of isoflavones to saponins is selected from the range of about 1:10 to about 10:1.

3. The composition of clam 1 in which the isoflavones are present in an amount form approximately 5% to approximately 90% by weight.

4. The composition of claim 1 in which said medicament is in a form of a product for oral delivery, said product form being selected from a group consisting of a concentrate, liquid, soft gel, dried powder, capsule, pellet, pill, suspensions, emulsions, and a food supplement including health bars.

5. The composition of claim 1 in which the lignans are present in an amount from about 1% to about 70% by weight.

6. The composition of claim 1 wherein said effective amount of said medicament is selected on a basis of a treatment for alcohol dependency.

7. The composition of claim 1 wherein the composition comprises between about 15% and about 25% by weight of the medicament and between about 65% and about 85% by weight of a filler.

8. The composition of claim 1 wherein said isoflavone is selected from a group consisting of malonyl, acetyl, glucoside; and aglycone.

9. The composition of claim 1 wherein the composition comprises:
   a. between about 15% and about 25% by weight of the medicament;
   b. between about 60% and about 84% be weight of a filler; and
   c. between about 1% and about 25% by weight of a dietary supplemental nutrient.

10. The composition of claim 1 wherein said isoflavone is concentrated for delivery in an easy to consume dosage.

* * * * *